United States Patent [19]

Thunberg

[11] Patent Number: 5,338,530

[45] Date of Patent: * Aug. 16, 1994

[54] RECOVERY OF GLYCINE AND GLAUBER'S SALT FROM WASTE CRYSTAL LIQUORS

[75] Inventor: Jon C. Thunberg, Milford, N.H.

[73] Assignee: Hampshire Chemical Corp., Lexington, Mass.

[*] Notice: The portion of the term of this patent subsequent to Jan. 22, 2008 has been disclaimed.

[21] Appl. No.: 612,660

[22] Filed: Nov. 9, 1990

Related U.S. Application Data

[63] Continuation of Ser. No. 336,366, Aug. 11, 1989, Pat. No. 4,986,976.

[51] Int. Cl.$^5$ .................................................. C01D 5/00
[52] U.S. Cl. ..................................... 423/551; 423/544; 562/554; 562/575; 23/302 T
[58] Field of Search ............... 423/544, 551, 193; 562/565, 566, 554, 575; 23/302 T

[56] References Cited

U.S. PATENT DOCUMENTS

| | | | |
|---|---|---|---|
| 3,510,515 | 5/1970 | Colburn | 562/554 |
| 3,808,269 | 4/1974 | Bragdon | 562/554 |
| 3,852,344 | 12/1974 | Bragdon et al. | 260/534 E |
| 3,904,585 | 9/1975 | Thunberg | 562/554 |
| 3,932,501 | 1/1976 | Thunberg | 562/554 |
| 3,947,496 | 3/1976 | Thunberg | 260/534 R |
| 3,985,801 | 10/1976 | Thunberg | 260/534 R |
| 4,299,978 | 11/1981 | Nakayasu et al. | 562/554 |
| 4,306,880 | 12/1981 | Garrett | 23/295 S |
| 4,691,054 | 9/1987 | Tosa et al. | 562/554 |
| 4,818,409 | 4/1989 | Pueter et al. | 210/638 |
| 4,986,976 | 1/1991 | Thunberg | 423/551 |
| 5,011,988 | 4/1991 | Thunberg | 562/554 |

FOREIGN PATENT DOCUMENTS

| | | | |
|---|---|---|---|
| 0081063 | 6/1983 | European Pat. Off. | 423/513 |
| 1493723 | 9/1967 | France | 423/513 |
| 53-13609 | 5/1978 | Japan | 562/575 |
| 56-73620 | 6/1981 | Japan | 423/551 |
| 1472840 | 9/1975 | United Kingdom . | |

*Primary Examiner*—Gary P. Straub
*Assistant Examiner*—Timothy C. Vanoy
*Attorney, Agent, or Firm*—Nields & Lemack

[57] ABSTRACT

Glycine and sodium sulfate decahydrate are separated from a starting aqueous solution containing glycine, sodium sulfate, and impurities, by forming a slurry which is a solid mixture of glycine and sodium sulfate decahydrate, followed by separation of the mixed crystals.

30 Claims, No Drawings

RECOVERY OF GLYCINE AND GLAUBER'S SALT FROM WASTE CRYSTAL LIQUORS

This is a continuation of U.S. application Ser. No. 07/336,366, filed Apr. 11, 1989, now U.S. Pat. No. 4,986,976.

BACKGROUND OF THE INVENTION

1. Field of the Invention

This invention relates to the recovery of glycine and Glauber's Salt ($Na_2SO_4.10H_2O$) from solutions such as the liquor generated in the process of producing glycine.

2. Description of the Prior Art

Typical prior art processes for the recovery of glycine from sodium sulfate solutions are disclosed in U.S. Pat. Nos. 3,904,585 and 3,947,496.

U.S. Pat. No. 3,904,585, the disclosure of which is herein incorporated by reference, discloses a process of recovering glycine or B-alanine from a starting aqueous solution of sodium sulfate and the amino acid having a temperature above about 33° C., a pH of 4.5–8.5, a mole ratio of amino acid to sodium sulfate of about 1–5:1 and containing at least 5% amino acid. The process comprises forming a first slurry without precipitating the amino acid, (the first slurry being a mixture of precipitated sodium sulfate and first mother liquor), by evaporating water from the starting solution while maintaining its temperature within a range (from 60° or 70° C. up to the normal boiling point) effective for preventing the precipitation of the amino acid, separating the first mother liquor from the precipitated sodium sulfate, cooling the separated first mother liquor to a temperature within a range (33°–40° C.) effective for precipitating the amino acid, and separating and recovering the precipitated amino acid.

U.S. Pat. No. 3,947,496, the disclosure of which is herein incorporated by reference, disclosures a process for recovering glycine from an aqueous starting solution of glycine and sodium sulfate that is similar to the process of the 3,904,585 patent. The process comprises cooling the aqueous starting solution to a temperature above about 33° C. so that glycine is precipitated, and separating and recovering the precipitated glycine. Further steps include precipitating anhydrous sodium sulfate by evaporating water from the separated first mother liquor, etc.

The foregoing references use processes where the temperature is specified to be 33° C. or higher so as to avoid the precipitation of sodium sulfate decahydrate with the amino acid. These processes generate waste liquor streams which include a substantial amount of product. Impurities generated in the glycine production process, for example, are removed as a waste purge stream taken from the glycine mother liquor tank. The primary constituents of this stream are glycine, imiodiacetic acid (IDA) monosodium salt, $Na_2SO_4$, and water. A typical composition is about 18% glycine, 11% IDA expressed as $IDAH_2$, 12% $Na_2SO_4$, with the balance being water and unidentified organic compounds. Streams such as this have heretofore been discarded.

Other approaches to the recovery of amino acids include U.S. Pat. No. 3,510,575 where glycine is separated from $NH_4Cl$, U.S. Pat. No. 4,691,575 where amino acids are isolated by ion exchange from systems that are substantially free of inorganic ions (such as sodium sulfate), and U.S. Pat. No. 4,299,978 where the mother liquor after separation of glycine is acidified to isolate IDS bisulfate, and the new mother liquor formed is recycled to the process. Glauber's Salt is not generated.

SUMMARY OF THE INVENTION

The problems of the prior art have been overcome by the present invention which provides a process for separating glycine and sodium sulfate decahydrate (Glauber's Salt) from amino carboxylate containing solutions such as the waste liquors generated from the production of glycine.

It is therefore an object of the present invention to provide a process of minimize generation of waste from the production of glycine.

It is a further object of the present invention to provide a process for the recovery of value from the waste generated from the production of glycine.

It is still further object of the present invention to provide a process which reduces disposal costs in the productions of glycine.

According to the present invention, these and other objects which will become more apparent, are accomplished by providing a process for separating and recovering glycine and sodium sulfate decahydrate from a liquor containing glycine and sodium sulfate, which entails forming a slurry of precipitated glycine, sodium sulfate decahydrate and mother liquor, by, for example, adjusting the temperature of the liquor to a level sufficient to crystallize the glycine and Glauber's Salt, followed by separation of the mixed crystals from the mother liquor. The mixed crystals can be recycled to a point in the glycine production process.

DETAILED DESCRIPTION OF THE PREFERRED EMBODIMENT

The process of preparing glycine from the corresponding nitrile can be accomplished according to the following sequence of reactions:

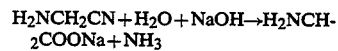

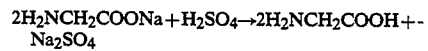

About 45% of the glycine now sent to waste in the glycine purge liquor from the foregoing process can be recovered, and at least a portion optionally recycled, in the process of the present invention. This can be accomplished by either batch or continuous cooling crystallization of the purge liquor to a temperature effective for precipitating the glycine and Glauber's Salt. In the batch process, solutions containing glycine, sodium sulfate, and impurities, such as waste liquor and recycled liquor produced in the process for the production of glycine, are charged to a cooling crystallizer. The mixture is cooled to a temperature effective for precipitating the glycine and Glauber's Salt. Glauber's Salt seed crystals can be added at about the saturation temperature of sodium sulfate decahydrate in the solution. Similarly, glycine seed crystals can be added to the solution. The recovered solid, which is a mixed wet cake comprising glycine and Glauber's Salt, is separated from the mother liquor by, for example, centrifugration. The solid can be recycled to n earlier point in the production process. For example, in the production process disclosed in U.S. Pat. No. 3,904,585, the solid can be recycled to the first slurry formation step. At least a portion of the mother liquor (e.g., 50%) can be recycled to the purge crystallizer to reduce the slurry density.

In another embodiment, a continuous crystallization can be used. A slurry of glycine, Glauber's Salt and liquor is prepared at the operating temperature (e.g., about 5° C.) by any suitable means. The primary consideration is to generate an initial slurry before continuous operation can start. One method for start-up is to charge the crystallizer with warm liquor (e.g., 40° C.) and slowly reduce the temperature, as in the batch mode. Glycine seed can be added in the beginning, and Glauber's Salt seed at about 18° C. As the slurry thickens upon further cooling, separation is begun (e.g., by centrifugration), with a portion of the liquor (e.g., 50%), being recycled to the crystallizer to maintain a manageable slurry density. Once the system is equilibrated at the operating temperature (e.g., 5° C.), continuous addition of fresh waste liquor is fed into the slurry (for example, directly into the crystallizer or into the stream feeding the crystallizer) while cooling to maintain the operating temperature. Both the glycine and Glauber's Salt crystallize, since the crystallizer operates at a temperature below the saturation temperature of both. Slurry is constantly withdrawn and subjected to separation. A portion of the liquor can be continuously recycled to the crystallizer to reduce the slurry density.

It is important that the entrainment of liquor in the wet cake be kept to a minimum, since this liquor is rich in impurities which should not be recycled to the glycine or $Na_2SO_4$ crystallizers in the glycine production process. The glycine:IDA weight ratio of the cake is a measure of the entrained liquor. Although a weight ratio of about 5:1 is operable, a ratio of at least about 10:1 is preferred to avoid recycle of excessive amounts of impurities, and is similar to that ratio in the incoming sodium glycinate. Any ratio greater than 10:1 can be used.

Separation is preferably accomplished by centrifugration, although other forms of separation such as filtration or decantation could be used. Suitable centrifuges include the traditional vertical perforated bowl centrifuge, which provides excellent separation of entrained liquor. A speed setting corresponding to a centrifugal force of about 500 g can be used. A setting corresponding to a centrifugal force of more than about 1000 g is preferred, with a force of about 2000 g being most preferable.

In the glycine production process, wash water can be used to wash the cake generated in the glycine production step free of sodium sulfate. However, this wash causes about 25–30% of the glycine in the cake to redissolve, which increases the glycine:IDA ratio in the mother liquor purge stream that can be the feedstock for the instant process. By excluding the wash water, the glycine:IDA ratio in the purge stream is minimized, thereby increasing the recovery of glycine by about 2% in the instant process. If such a concentrated purge is used, it can be diluted with water to adjust the total solids level to a range of about 40%–50%. A total solids level of about 48–54% is preferred, with a level of about 52% being especially preferred.

The temperature at which glycine and Glauber's Salt are precipitated is a function of the concentration of glycine and the sodium sulfate in the solution. The typical waste purge stream from the process for the production of glycine has a composition of about 18% glycine and about 12% sodium sulfate. The preferred temperature to which such a solution should be cooled is about 5° C. Those skilled in the art will be able to determine the necessary temperature to which the particular stream must be cooled to precipitate glycine and Glauber's Salt.

A glycine stream having the aforementioned composition precipitates because of the decreased solubility at about 5° C. as compared to its solubility in the starting solution, which has a temperature of about 40° C. Simultaneously, solute (i.e., water) is removed with the $Na_2SO_4$, which crystallizes as $Na_2SO_4 10H_2O$. Because this water becomes part of the solids in the slurry, the slurry density becomes high. In the continuous system, the slurry density can be adjusted appropriately by continuously recycling saturated 5° C. mother liquor back to the crystallizer.

The recovered solid, which is a mixture of glycine, Glauber's Salt, plus some entrained liquor, can be recycled to the mix tank that contains the feed to the $Na_2SO_4$ crystallizer in the glycine production process. Water is added to the solid to create a pumpable stream. From that crystallization, the $Na_2SO_4$ is isolated as anhyrous $Na_2SO_4$. The mother liquor remaining after separation of the $Na_2SO_4$ contains the glycine which is then crystallized in the succeeding glycine crystallizer. A portion of the mother liquor remaining after separation of glycine is the purge liquor feed stock (with or without wash) for the present process.

The instant invention will be better understood by referring to the following specific but non-limiting examples. It is understood that said invention is not limited by these procedures which are offered merely as illustrations; it is also understood that modifications can be made without departing from the spirit and scope of the invention.

EXAMPLE 1

The typical purge liquor generated in the glycine production process has a starting temperature of about 40° C. A study of the cooling rate was conducted in a batch cooling crystallizer where 1200 grams of purge (composition: 18.8% glycine, 11.4% $IDAH_2$, 10.6% $Na_2SO_4$) was equilibrated at 40° C., seeded with 25 grams of mixed seed, and linearly program-cooled to 5° C. at rates of 2.19° C./hr, 5.83° C./hr, and 17.5° C./hr. Experiments cooling slurries to 10° C. and 15° C. also were run. Slurries cooled to 5° C. using cooling rates of either 2.19° C./hr or 5.83° C./hr produced clean cakes which were indistinguishable. The slurry cooled at the rate of 17.5° C./hr produced a sticky wet cake. The analysis of the slurries cooled at 2.19° C./hr and 5.83° C./hr is shown below:

|  | Air Dried Solid From Cooling Rates of: | |
| --- | --- | --- |
|  | 2.19C.°/hr (16 Hr) | 5.83C.°/hr (6 hr) |
| Recovery of Glycine from the Feed | 61% | 60% |
| % Glycine | 54.7% | 54.1% |
| % IDA $H_2$ | 6.6% | 7.5% |
| Glycine:$IDAH_2$ Ratio | 8.28:1 | 7.21:1 |

The saturation temperature of Glauber's Salt in the glycine purge slurry was determined to be about 18°–20° C. Material crystallized by adding $Na_2SO_4 10$-$H_2O$ seed at about the saturation temperature produced uniform, easily centrifuged slurries without thixotropic properties.

EXAMPLE 2

Glycine can be isolated as the acid salt Triglycine Sulfate (Glycine)$_3$.H$_2$SO$_4$, at low pH. A glycine-containing purge containing 18.8% glycine, 11.4% IDAH$_2$, and 10.6% Na$_2$SO$_4$ was acidified with 25.6g of 93% H$_2$SO$_4$. to lower the pH to 3.0, and with 226 g of 93% H$_2$SO$_4$ to lower the pH to 2.0, seeded with (gly)$_3$.H$_2$SO$_4$ and cooled to 5° C. over 6 hr. The pH 2.0 slurry had to be centrifuged at approximately 23° C. as well as 5° C. to maintain a workable slurry density. Table I shows the results:

TABLE I

|  | Air Dried Solid From | |
|---|---|---|
|  | pH 3.0 | pH 2.0 |
| % of Glycine Recovered | 35% | 64% |
| % Glycine | 27.8% | 32.5% |
| % IDA H$_2$ | 3.0% | 15.7% |

The solid was heavily contaminated with IDA and required a large consumption of Na$_2$SO$_4$. Accordingly, lowering of the pH is not practical unless such considerations are not deleterious to the intended application.

EXAMPLE 3

Batch Crystallization of Glycine Purge Liquor 1250 g of glycine purge containing 19.8% glycine and 12.9% Na$_2$SO$_4$, was diluted with 60 g of water to reduce the total solids content to 52.0%. This solution was charged to a 1 liter batch cooling crystallizer. The temperature was equilibrated at 40° C. and then seeded with 10 g of glycine. The mixture was linearly cooled to 5° C. over 4 hr. The slurry was seeded with 5 g of Glauber's Salt at 18° C. to initiate crystallization of this salt. The solid was recovered with a centrifuge operating at about 550 g. 311 g of air-dried solid was recovered which contained 37.7% glycine and 49.4% Na$_2$SO$_4$, which represented recoveries of 50% and 82%, respectively.

EXAMPLE 4

Continuous Crystallization of Glycine Purge Liquor

A 1 liter batch crystallization was run as described in Example 3 and mixed with an approximately equal amount of liquor generated from previous experiments. This mixture, chilled to 5° C., was charged to a 2 liter crystallizer. Fresh 40° C. glycine purge liquor was continually pumped into the crystallizer at a rate of about 24 g/min; this gave an average residence time in the crystallizer of 2 hr. The crystallizer was continually cooled to maintain the slurry at 5° C.

When the slurry level reached maximum, about 25% of the slurry was pumped directly into a centrifuge. The centrate was collected in a fared beaker, weighed, and then 50% of the collected centrate was added back to the crystallizer. The pre-tared centrifuge basket was weighed and the collected solids were scraped into a dish and air dried. The solids were later dried under vacuum at 60° C.

This process was continued without interruption for 24 hr, or a total of about 12 residence times. Over the course of this experiment, 34.3 kg of purge liquor was charged and 12.9 kg of wet solid was recovered. The average composition of the wet solids was 42.6% glycine and 44.1% Na$_2$SO$_4$, representing recoveries of 49% and 78%, respectively.

What is claimed is:

1. A process for separating glycine and sodium sulfate decahydrate crystals from a starting aqueous solution comprising glycine and sodium sulfate, said process comprising the steps of:
   a. precipitating a solid mixture of glycine and sodium sulfate decahydrate in the same mother liquor; and
   b. separating the solid mixture from the mother liquor.

2. A process according to claim 1, wherein the precipitate is formed by lowering the temperature of the starting aqueous solution.

3. A process according to claim 1 comprising the further step of recycling separated mother liquor to step a.

4. A process according to claim 1 further comprising adding glycine seed crystals to said starting aqueous solution prior to step a at a temperature and in an amount sufficient to initiate glycine precipitation during step a.

5. A process according to claim 1 further comprising adding sodium sulfate decahydrate seed crystals during the formation of the slurry in step a in an amount sufficient to initiate sodium sulfate decahydrate precipitation.

6. A process according to claim 1 further comprising adding sodium sulfate decahydrate seed crystals during the formation of the slurry in step a at a temperature and in an amount sufficient to initiate sodium sulfate decahydrate precipitation.

7. A process according to claim 6 wherein the sodium sulfate decahydrate seed crystals are added at about the saturation temperature of sodium sulfate decahydrate in said starting aqueous solution.

8. A process according to claim 1, wherein said starting solution has a temperature of about 40° C. prior to step a.

9. A process according to claim 2, wherein the temperature is adjusted at a cooling rate of about 5.8° C./hr.

10. A process according to claim 2 wherein said solution is cooled to a temperature of about 5° C.

11. A process according to claim 1 wherein the starting solution has a total solids level of about 48–54%.

12. A process for separating glycine and sodium sulfate decahydrate crystals from a starting aqueous solution comprising glycine and sodium sulfate, said process comprising the steps of:
   a. cooling said solution to a temperature effective for precipitating a solid mixture of glycine and sodium sulfate decahydrate in the same mother liquor; and
   b. separating the solid mixture from the mother liquor.

13. A process according to claim 12 comprising the further step of recycling separated mother liquor to step a.

14. A process according to claim 12 further comprising adding glycine seed crystals to said starting aqueous solution prior to step a at a temperature and in an amount sufficient to initiate glycine precipitation during step a.

15. A process according to claim 14 wherein said seed crystals are added at about the saturation temperature of glycine in said solution.

16. A process according to claim 12 further comprising adding sodium sulfate decahydrate seed crystals during the cooling step at a temperature and in an amount sufficient to initiate sodium sulfate decahydrate precipitation.

17. A process according to claim 16 wherein the sodium sulfate decahydrate seed crystals are added at about the saturation temperature of sodium sulfate decahydrate in said starting aqueous solution.

18. A process according to claim 12, wherein said starting solution has a temperature of about 40° C. prior to the cooling step.

19. A process according to claim 12, wherein the cooling step is carried out at a cooling rate of about 5.8° C./hr.

20. A process according to claim 12 wherein said solution is cooled to a temperature of about 5° C.

21. A process according to claim 12 wherein the starting solution has a total solids level of about 48–54%.

22. A process for precipitating glycine and sodium sulfate decahydrate from a starting aqueous solution containing glycine and sodium sulfate, said solution having a temperature of about 40° C., said process comprising:
 a. cooling the solution to a temperature effective for precipitating glycine and sodium sulfate decahydrate in the same mother liquor;
 b. during said cooling step adding sodium sulfate decahydrate seed crystals at about the sodium sulfate decahydrate saturation temperature of said solution; and
 c. separating the precipitate.

23. A process according to claim 22 further comprising adding glycine seed crystals prior to step a at a temperature and in an amount sufficient to precipitate glycine during step a.

24. A process according to claim 22 wherein said separation is accomplished by centrifugration.

25. A process for the continuous separation of glycine and sodium sulfate decayhdration crystals from an aqueous solution comprising glycine and sodium sulfate, comprising:
 a. preparing a slurry which is a mixed precipitate comprising glycine and sodium sulfate decahydrate in the same liquor at about the temperature specified in step c;
 b. feeding said slurry into a crystallizer;
 c. feeding said aqueous solution comprising glycine and sodium sulfate into said slurry while cooling to maintain the temperature at a level effective for precipitating glycine and sodium sulfate decahydrate; and
 d. withdrawing said slurry and separating glycine and sodium sulfate decahydrate therefrom.

26. The process of claim 25 wherein the residence time of said solution in said crystallizer is about two hours.

27. The process of claim 25 further comprising recycling liquor resulting from said separation to said crystallizer.

28. The process of claim 25 wherein the solution of glycine and sodium sulfate has a total solids level of about 48–54%.

29. The process of claim 25 wherein the aqueous solution in step c is fed into the slurry in the crystallizer.

30. The process of claim 25 wherein the aqueous solution in step c is fed into the slurry at a point prior to where said slurry enters said crystallizer.

* * * * *